(12) United States Patent
Murai et al.

(10) Patent No.: US 6,703,410 B1
(45) Date of Patent: Mar. 9, 2004

(54) CRYSTAL FORMS OF 3-(2,4-DICHLOROBENZYL)-2-METHYL-N-(PENTYLSULFONYL)-3H-BENZIMIDAZOLE-5-CARBOXAMIDE

(75) Inventors: Yoshiyuki Murai, Hyogo (JP); Noritsugu Yamasaki, Hyogo (JP); Takafumi Imoto, Niigata (JP); Masahiro Nishikawa, Niigata (JP); Kunihiko Dohtsu, Hyogo (JP)

(73) Assignees: Fujisawa Pharmaceutical Co., Ltd., Osaka (JP); Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/831,082

(22) PCT Filed: Nov. 11, 1999

(86) PCT No.: PCT/JP99/06296
§ 371 (c)(1),
(2), (4) Date: Sep. 13, 2001

(87) PCT Pub. No.: WO00/29383
PCT Pub. Date: May 25, 2000

(30) Foreign Application Priority Data

Nov. 13, 1998 (JP) .......................................... 10/324026

(51) Int. Cl.[7] ................... A61K 31/4184; C07D 235/08
(52) U.S. Cl. .................. 514/394; 548/304.4; 548/310.4
(58) Field of Search ........................... 548/304.4, 310.4; 514/394

(56) References Cited

U.S. PATENT DOCUMENTS 6,166,219 A    12/2000   Yamasaki et al.

FOREIGN PATENT DOCUMENTS

| AU | 199712095 B2 | 7/1997 |
| EP | 1 132 087 A1 | 9/2001 |
| HU | 9801692 | 5/1999 |
| WO | WO 96/33194 | 10/1996 |

*Primary Examiner*—Laura L. Stockton
(74) *Attorney, Agent, or Firm*—Fish & Richardson P.C.

(57) ABSTRACT

3-(2,4-Dichlorobenzyl)-2-methyl-N-(pentylsulfonyl)-3H-benzimidazole-5-carboxamide, a compound having hypoglycemic activity or PDE5 inhibitory effect, has three forms of crystal forms that are distinguishable by their X-ray powder diffraction values. The most crystallographically stable crystal form is useful as a drug substance for medicines. Another crystal form can be purified efficiently by crystallization, since it forms larger crystals and can be very easily isolated by filtration. Thus this crystal form is useful for purifying 3-(2,4-Dichlorobenzyl)-2-methyl-N-(pentylsulfonyl)-3H-benzimidazole-5-carboxamide.

13 Claims, 6 Drawing Sheets

CRYSTAL FORMS OF 3-(2,4-DICHLOROBENZYL)-2-METHYL-N-(PENTYLSULFONYL)-3H-BENZIMIDAZOLE-5-CARBOXAMIDE

TECHNICAL FIELD

The present invention relates to crystal forms of 3-(2,4-dichlorobenzyl)-2-methyl-N-(pentylsulfonyl)-3H-benzimidazole-5-carboxamide having hypoglycemic activity or a PDE5 inhibitory effect, and a method for manufacturing the same.

BACKGROUND ART

When a compound containing crystal polymorphs is used as a medicine, it is often necessary to produce a drug substance having a specific crystal form to guarantee the consistency of physicochemical and biological properties of the compound. Futhermore, in the process of manufacturing a drug substance, it is often important to separate out a particular form of crystal during the crystallization procedure, in order to maintain defined levels of the yield and purification efficiency.

3-(2,4-Dichlorobenzyl)-2-methyl-N-(pentylsulfonyl)-3H-benzimidazole-5-carboxamide has been disclosed as a benzimidazole compound having hypoglycemic activity or PDE5 inhibitory effect in WO97/24334 (cf. Example 251). However, the existence of crystal polymorphs of this compound has not hitherto been recognized, nor has a substantially and crystallographically pure crystal of this compound having a particular form been obtained.

DISCLOSURE OF THE INVENTION

It is an object of this invention to provide a substantially and crystallographically pure crystal form of 3-(2,4-dichlorobenzyl)-2-methyl-N-(pentylsulfonyl)-3H-benzimidazole-5-carboxamide that is useful as a medicine, a method for manufacturing the same, and a medical composition comprising the same.

The present inventors studied various conditions for crystallizing 3-(2,4-dichlorobenzyl)-2-methyl-N-(pentylsulfonyl)-3H-benzimidazole-5-carboxamide. As a result, they found three forms of crystals in this compound. Herein, these three crystal forms are referred to as crystal forms A, B and C. The inventors also discovered that crystal forms A and B have advantages over other crystal forms, respectively. That is, crystal form A is crystallographically more stable than crystal form B and C, though it forms smaller crystals. It is thus more easily obtainable as substantially and crystallographically pure crystals, which is favorable for maintaining the quality of a pharmaceutical preparation as a medicine. On the other hand, crystal form B, while not as crystallographically stable as crystal form A, forms larger crystals than crystal form A, so that it can be isolated with greater ease, by filtration, and efficiently purified, by crystallization.

Furthermore, the present inventors found that each crystal form can be obtained in a substantially pure crystallographic form and in an industrially stable manner, by using a crystallization method preferable for the respective form, thereby accomplishing the present invention.

Thus, this invention relates to (1) a substantially and crystallographically pure crystal form of 3-(2,4-dichlorobenzyl)-2-methyl-N-(pentylsulfonyl)-3H-benzimidazole-5-carboxamide having the following X-ray powder diffraction values (2θ), with an error range of ±0.2, in an X-ray powder diffraction assay using CuKα-ray as a characteristic X-ray:

Angle 2θ(°): about 4.7, about 9.5, about 10.5, about 15.6, and about 18.4; and (2) a substantially and crystallographically pure crystal form of 3-(2,4-dichlorobenzyl)-2-methyl-N-(pentylsulfonyl)-3H-benzimidazole-5-carboxamide having the following X-ray powder diffraction values (2θ), with an error range of ±0.2, in an X-ray powder diffraction assay using CuKα-ray as a characteristic X-ray:

Angle 2θ(°): about 4.4, about 8.9, and about 13.4.

The present invention also relates to a pharmaceutical composition comprising crystal form of 3-(2,4-dichlorobenzyl)-2-methyl-N-(pentylsulfonyl)-3H-benzimidazole-5-carboxamide described in (1) as an active ingredient. The present invention also relates to a pharmaceutical composition comprising crystal form of 3-(2,4-dichlorobenzyl)-2-methyl-N-(pentyl-sulfonyl)-3H-benzimidazole-5-carboxamide described in (2) as an active ingredient.

The present invention further relates to a process for producing crystal form (1) above, which comprises crystallization of 3-(2,4-dichlorobenzyl)-2-methyl-N-(pentylsulfonyl)-3H-benzimidazole-5-carboxamide from an organic solvent or a mixture of an organic solvent and water. The present invention also relates to a process for producing crystal form (2) above, which comprises crystallization of 3-(2,4-dichlorobenzyl)-2-methyl-N-(pentylsulfonyl)-3H-benzimidazole-5-carboxamide by adding acid to the solution of 3-(2,4-dichlorobenzyl)-2-methyl-N-(pentylsulfonyl)-3H-benzimidazole-5-carboxamide dissolved in an organic solvent or a mixture of an organic solvent and water in the presence of alkali.

As used herein, the term "substantially and crystallographically pure" means that other crystal forms are not analytically identifiable. In this context, analysis refers to at least one of powder X-ray diffraction, infrared spectrophotometry (IR) and thermogravimetry/differential thermal analysis (TG/DTA), which are described below.

Crystal form A of 3-(2,4-dichlorobenzyl)-2-methyl-N-(pentylsulfonyl)-3H-benzimidazole-5-carboxamide (often referred to as Compound (I) hereafter) is characterized as having the following X-ray powder diffraction values (2θ), with an error range of ±0.2, in an X-ray powder diffraction assay using CuKα-ray as the characteristic X-ray:

Angle 2θ(°): about 4.7, about 9.5, about 10.5, about 15.6, and about 18.4.

More specifically, for example, crystal form A shows the following diffraction values.

| Angle 2θ (°) | Relative intensity I/Imax (%) |
|---|---|
| 4.7 | 67 |
| 9.5 | 45 |
| 10.5 | 21 |
| 15.6 | 58 |
| 16.2 | 19 |
| 18.4 | 100 |
| 19.1 | 21 |
| 20.6 | 93 |
| 21.4 | 29 |
| 22.9 | 58 |
| 23.4 | 30 |
| 24.0 | 14 |
| 24.7 | 10 |
| 25.2 | 27 |
| 26.4 | 31 |
| 27.6 | 31 |
| 28.9 | 10 |
| 29.1 | 11 |

-continued

| Angle 2θ (°) | Relative intensity I/Imax (%) |
|---|---|
| 30.8 | 27 |
| 32.9 | 37 |

Crystal form B of Compound (I) is characterized as having the following X-ray powder diffraction values (2θ), with an error range of ±0.2, in an X-ray powder diffraction assay using CuKα-ray as a characteristic X-ray:

Angle 2θ(°): about 4.4, about 8.9, and about 13.4.

More specifically, for example, crystal form B shows the following diffraction values.

| Angle 2θ (°) | Relative intensity I/Imax (%) |
|---|---|
| 4.4 | 58 |
| 8.9 | 65 |
| 10.8 | 49 |
| 13.4 | 47 |
| 14.0 | 44 |
| 17.8 | 39 |
| 18.2 | 12 |
| 18.9 | 33 |
| 19.3 | 35 |
| 20.1 | 18 |
| 20.9 | 24 |
| 21.4 | 100 |
| 21.7 | 94 |
| 22.4 | 30 |
| 23.2 | 38 |
| 24.0 | 19 |
| 24.6 | 45 |
| 24.8 | 53 |
| 26.1 | 41 |
| 27.1 | 57 |
| 27.8 | 14 |
| 28.3 | 11 |
| 29.6 | 12 |
| 30.5 | 15 |
| 31.7 | 14 |
| 36.1 | 15 |
| 38.3 | 15 |

Furthermore, crystal form C of Compound (I) has the following X-ray powder diffraction values (2θ), with an error range of ±0.2, in an X-ray powder diffraction assay using CuKα-ray as a characteristic X-ray:

| Angle 2θ (°) | Relative intensity I/Imax (%) |
|---|---|
| 8.0 | 27 |
| 9.3 | 100 |
| 11.9 | 12 |
| 12.5 | 30 |
| 14.9 | 63 |
| 18.8 | 16 |
| 20.2 | 38 |
| 22.1 | 24 |
| 22.9 | 26 |
| 23.9 | 39 |
| 25.2 | 30 |
| 25.6 | 11 |
| 26.3 | 27 |
| 27.2 | 13 |
| 29.0 | 25 |
| 29.9 | 17 |

The X-ray powder diffraction values (2θ) described above were determined using the following apparatus and conditions:

Apparatus: Rigaku RINT-1500 (Rigaku Denki Kogyo Inc.);

Characteristic X-ray: CuKα rays (using a monochrometer);

Tube electric current/tube voltage: 40 kV/30 mA;

Detector: proportional counter;

Scanning speed: 2θ=3°–40°; and

Slit system: divergence slit, 1°; scattering slit, 1°; receiving slit 0.3 mm.

Crystal forms A, B and C of Compound (I) can also be discriminated by IR spectra. The significantly different peaks in the absorption pattern for each crystal form in IR (KBr) spectra, determined by infrared spectrophotometric analysis (KBr disk method), are contrasted in the following table:

| Crystal form A ($cm^{-1}$) | Crystal form B ($cm^{-1}$) | Crystal form C ($cm^{-1}$) |
|---|---|---|
|  |  | 3553 |
| 1673 | 1692 | 1690 |
| 1513 | 1520 | 1518 |
| 1463 | 1497 | 1496 |
| 1449 | 1470 | 1465 |
| 1409 | 1454 | 1447 |
| 1384 | 1404 | 1408 |
|  | 1392 |  |
| 1345 | 1354 | 1348 |
| 1329 | 1337 | 1335 |
| 1318 |  |  |
| 1157 | 1163 | 1146 |
| 1145 | 1148 | 1113 |
| 1128 | 1114 |  |
| 892 | 892 | 882 |
| 870 | 880 | 865 |
| 842 | 868 | 849 |
|  | 850 | 836 |
|  | 833 |  |

The IR spectra shown above were obtained using the following apparatus and conditions described below.

Apparatus: PERKIN ELMER 1650 FT-IR (Perkin-Elmer, Japan);

Measuring method: KBr-disk method; and

Disk: 3 mm in diameter.

IR data for each crystal form, determined by Nujol method, as well as for Compound (I), generated and purified according to a conventional method (WO97/24334), are shown in the following table:

| Crystal form A ($cm^{-1}$) | Crystal form B ($cm^{-1}$) | Crystal form C ($cm^{-1}$) | Compound (I) ($cm^{-1}$) |
|---|---|---|---|
| 1673 | 1693 | 1689 | 1682 |

In addition, crystal forms A, B and C of Compound (I) can also be distinguished by thermogravimetry/differential thermal analysis (TG/DTA) as described below:

Crystal form A: a maximum melting endotherm at the extrapolation initiation temperature of about 211° C.;

Crystal form B: a maximum transient endotherm at the extrapolation initiation temperature of about 186° C. and a maximum melting endotherm at the extrapolation initiation temperature of about 211° C.; and Crystal form C: a maximum melting endotherm at the extrapolation initiation temperature of about 102° C. and a subsequent maximum exotherm, a maximum melting endotherm at the extrapolation initiation temperature of about 211° C., and a 1–2% weight loss around the former maximum melting endotherm.

The aforesaid thermogravimetry/differential thermal analysis (TG/DTA) was determined with the apparatus and under the conditions as described below:

Apparatus: SII TG/DTA 6300 (Seiko Instruments Inc.);

Temperature condition: 30° C. (0 min)→10° C./min→350° C.;

Sample container: Al sealed container;

Atmosphere: $N_2$, 300 ml/min; and

Sampling time: 0.5 s.

A substantially and crystallographically pure crystal form A of Compound (I) can be manufactured in a stable manner by dissolving compound (I) in an organic solvent or a mixture of organic solvent and water, heating the solution, and then by putting this solution into crystallization during heating. For the solvent, a mixture of water and an organic solvent, including, but not limited to, amides (e.g. N,N-dimethylformamide, N,N-dimethylacetamide, etc.), alcohols (e.g. methanol, ethanol, 1-propanol, 2-propanol, etc.) and ketones (e.g. acetone, methylethyl ketone, etc.), is preferably used. One or more of these solvents can be combined in the mixed solvent. Among aqueous/organic solvent mixtures, a mixed solvent of a ketone and water is more preferred, and a mixed solvent of acetone and water is even more preferred.

Since solubility varies with the type and composition of solvent used, there is no particular limitation on the mixing rate of an organic solvent and water. When dissolving compound (I), a higher ratio of organic solvent to water has the advantage of giving improved solubility; the organic solvent to water ratio is preferably, from 100:0 to 50:50 (w/w), and more preferably, from 100:0 to 70:30 (w/w). When completing crystallization of compound (I), it is advantageous to reduce the ratio of the organic solvent in a relative manner in order to obtain a sufficient yield; the organic solvent to water ratio is preferably reduced to 95:5 to 5:95 (w/w), and more preferably to 90:10 to 30:70 (w/w).

To precipitate the crystals during heating, a poor solvent, such as water, is added to the solution of compound (I) in the aforesaid solvent during heating; alternatively, the organic solvent is evaporated. In addition, if compound (I) is maintained at high temperature, it is possible to precipitate the crystals by cooling.

In any method as described above, to obtain crystal form A, it is desirable to initiate the crystallization at 30° C. or higher. There is no defined upper limit of the initiation temperature since the solubility varies with type or composition of solvent used. The initiation temperature may be between 30° C. and the boiling point of the solvent employed, and below the solubility of crystal form A. Preferably, the crystallization is initiated at the temperature higher than 40° C. to more stably obtain crystal form A. In the context of the present invention, "initiation of crystallization" refers to the time any crystals start to be precipitated, if no seed crystals are added, or to the time any crystals other than seed crystals start to be precipitated if seed crystals are added.

Crystal form A of compound (I) can also be manufactured by maintaining a suspension containing compound (I), in any crystalline form or in amorphous form or a mixture thereof, in a solvent in the heat so as to induce the transition of crystal form in the suspended state.

In this instance, the heating temperature is not limited to a certain range, so long as it ensures the transition; however, it is desirable to retain a temperature of 30° C. or higher in order to obtain crystal form A in a stable manner. Again, there is no defined upper limit on the retention temperature since the solubility varies with the type or composition of solvent used. The retention temperature may be between 30° C. and the boiling point of the solvent employed, and also below the solubility of crystal form A. A retention temperature of 40° C. or higher is preferable to obtain crystal form A in a more stable manner.

There is no particular limitation on the retention time so long as it can ensure the transition; however, it is preferably at least five minutes, more preferably at least one hour. There is no defined upper limit on the retention time; however, from the economic point of view, it is preferably three days or less, more preferably one day or less.

Furthermore, it is also possible to combine the crystallization and transition methods above, although either can be employed singly, to obtain crystal form A. To reduce the possibility of crystallization of crystal forms other than desired crystal form of Compound (I) in these crystallization and transition methods, it may be effective to add a small amount of seed crystals of form A to the solution, for example, prior to the initiation of crystallization.

In order to increase the yield, crystals can be grown using seed crystals of form A already crystallized by further adding a poor solvent, such as water, or by cooling the solution after crystals have come out. After crystallization, the filtrate is removed by a conventional method, for example, centrifugation, filtration, and such, and the crystals are dried by a conventional drying method, such as vacuum drying or hot air drying, and such, to obtain the desirable crystal form A.

A substantially and crystallographically pure crystal form B of Compound (I) can be stably manufactured through crystallization of free Compound (I), by adding an acid to a salt solution of Compound (I) and a base.

The bases to form a salt with Compound (I) include, but are not limited to, inorganic bases (e.g. sodium hydroxide, potassium hydroxide, sodium carbonate, potassium carbonate, sodium methoxide, etc.), and organic bases (e.g. 4-N,N-dimethylaminopyridine, 1,8-diazabicyclo[5.4.0]-7-undecene, 1,5-diazabicyclo[4.3.0]-5-nonene, triethylamine, imidazole, etc.). These bases can be used alone or in combination, as a mixture.

It is not necessary to isolate the salt form of Compound (I) with a base beforehand. A salt solution of Compound (I) and a base can be prepared by adding base in an amount sufficient to dissolve the suspension of free Compound (I) in the solvent system used for crystallization, or by utilizing the base used in the condensation reaction as the base to form the salt form of Compound (I).

There is no limitation on the amount of the base so long as it is sufficient to dissolve Compound (I) completely in the solvent used for Compound (I) in the presence of the base. However, in general, the total amount of the base used is preferably half to 10-fold of the equivalent amount of Compound (I). More preferably, an equivalent amount to a 4-fold amount of base is used.

Acids to be used for neutralization include, but are not limited to, inorganic acids (e.g. hydrochloric acid, sulfuric acid, phosphoric acid, etc.) and organic acids (e.g. acetic acid, propionic acid, methane sulfonic acid, etc.) can be used. These acids can be used alone or in combination, as a mixture.

There is no limitation on the amount of the acid, so long as it is sufficient to generate free Compound (I), by neutralizing the base used for dissolution of compound (I), thereby precipitating crystal form B. Typically, the total amount of the acid applied is preferably 0.1- to 10-fold, and more preferably 0.2- to 2-fold the amount of the base used for dissolution of Compound (I).

There is no particular limitation on the types of solvents used for dissolution; organic solvents, water, or mixtures thereof may be used. There is no particular limitation on the types of organic solvents; however, from the perspective of solubility and operationality, they are exemplified by amides (e.g. N,N-dimethylformamide, N,N-dimethyl-acetamide, etc.), alcohols (e.g. methanol, ethanol, 1-propanol, 2-propanol, etc.) and ketones (e.g. acetone, methyl ethyl ketone, etc.). These solvents may be used singly or in combination, at any mixing ratios. For organic solvents, alcohols are preferable, and methanol is particularly preferable. In addition, in the case where an inorganic base or acid is used, it is preferable to include water as the solvent in order to remove salts generated.

To ensure crystallization and yield of crystal form B of Compound (I) in the crystallization process, a small amount of seed crystals of form B can be added to the solution.

Typically, the crystallization temperature is below the boiling point of the solvent used; however, the crystallization temperature varies with the solvent system used and the dissolubility thereof and, thus, is not specifically defined. However, this temperature is required to be within the range that can prevent transition to crystal form A of Compound (I) once crystal form B is crystallized.

When Compound (I) is dissolved in the presence of a base, and subsequently an acid is added to precipitate crystal form B, this form would exist as a relatively stable form even if it were suspended in a solvent. However, transition to crystal form A occurs if the temperature becomes too high or the retention time is extended for too long. Thus, it is necessary to prevent this transition in order to obtain crystal form B. The temperatures at which crystal form B transitions into crystal form A, and the retention times required to complete isolation will vary depending on the types and composition used for the process, as well as on the interaction between the temperature and retention time. Therefore, the temperature and retention time are not specifically defined. However, lower temperatures and shorter retention times are favorable. Typically, the retention temperature is preferably below the boiling point of the solvent, or 60° C. or below, and more preferably 55° C. or below. Also, typically, the retention time until completion of the isolation is preferably 5 days or less, and more preferably 2 days or less at the temperature of, for example, 50° C.

After crystallization, the filtrate is removed by a conventional method, for example, centrifugation, filtration, and such, and the crystals are dried by a conventional drying method such as vacuum drying, hot air drying, and such, to obtain the desirable crystal form B.

In addition, the present invention provides a pharmaceutical composition comprising the crystal form A of Compound (I), obtained as described above, as an active ingredient.

Compound (I) can be used for prevention or therapy of various diseases, on the basis of its hypoglycemic activity or PDE5 inhibitory effect. It is useful for treatment or prevention of diseases including, but not limited to, polycystic ovary syndrome, gestational diabetes, diabetic complications (diabetic osteopenia, osteoporosis), autoimmune diseases, pancreatitis, cachexia (progressive weight loss due to lipolysis, myolysis, anemia, edema, anorexia and the like) and in chronic diseases such as cancer, tuberculosis, endocrine diseases, and AIDS).

The pharmaceutical composition of the present invention may be prepared by mixing crystal form A of Compound (I) with a pharmaceutically acceptable carrier, such as an organic and inorganic vehicle, in a solid, semi-solid or liquid state suitable for oral, parenteral administration and external application (local application). The pharmaceutical composition may be in a solid form, such as tablet, granule, powder, capsule, dragee and suppository; in a liquid form, such as suspension, milky lotion, syrup, emulsion, lemonade, lotion, etc.; ointment; and gel. The above preparation may contain, if necessary, an auxiliary, stabilizer, wetting agent, emulsifier, buffer, and an ordinary additive, such as lactose, citrate, tartarate, stearate, magnesium stearate, clay, sucrose, corn starch, talc, gelatin, agar, pectin, peanut oil, olive oil, cacao oil, ethylene glycol, etc.

The dose of Compound (I) can be routinely determined, depending on the age and conditions of the patient, and the type and state of the disease. Typically, 1 to 100 mg/kg of compound (I) for oral administration, and 0.1 to 10 mg/kg for intramuscular or intravenous injection, administered one to four times a day.

BEST MODE FOR CARRYING OUT THE INVENTION

Figure 1:
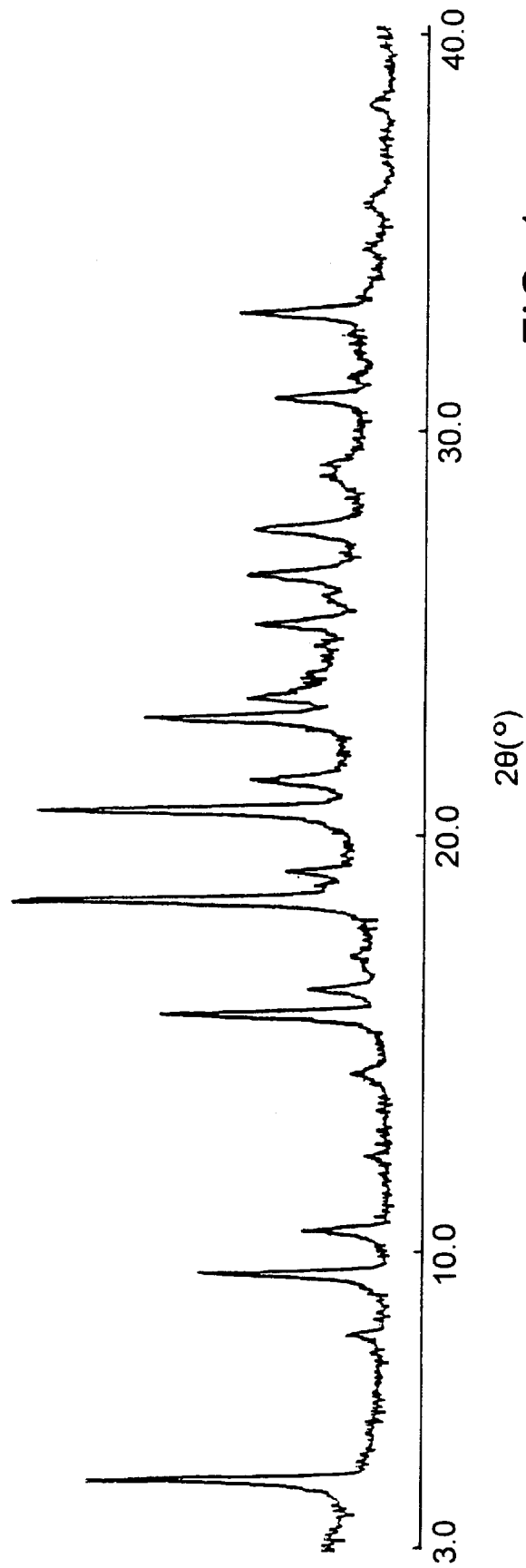
FIG. 1 shows an X-ray powder diffraction pattern of crystal form A of Compound (I).
Figure 2:
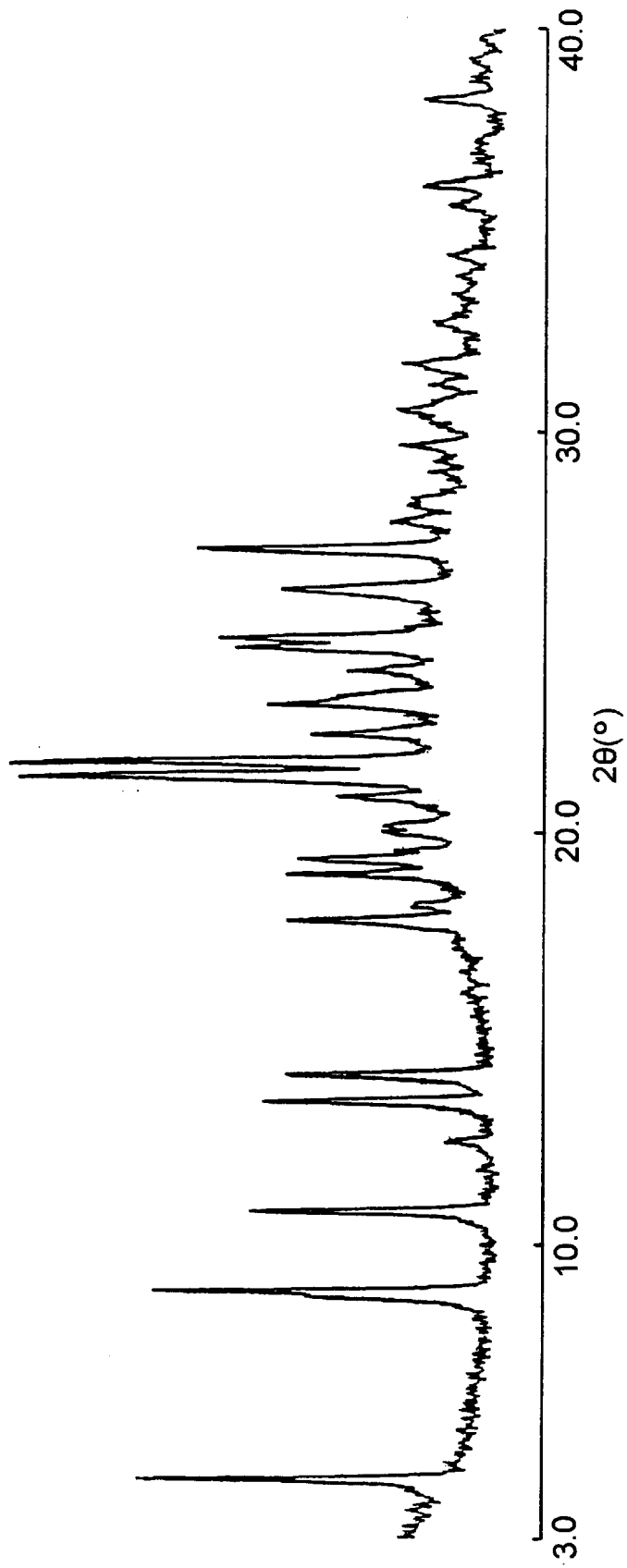
FIG. 2 shows an X-ray powder diffraction pattern of crystal form B of Compound (I).
Figure 3:
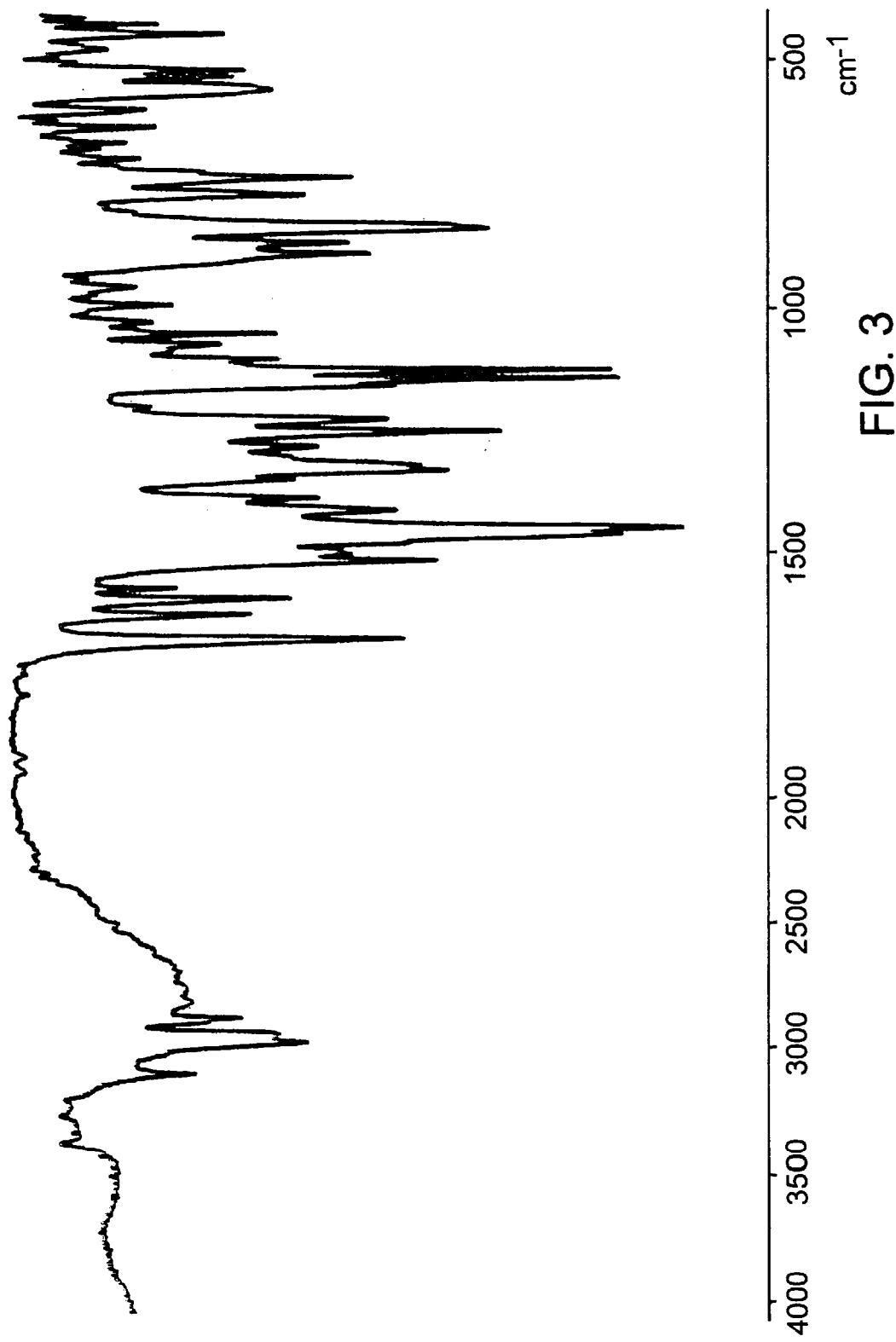
FIG. 3 shows an IR spectrum (KBr disk method) of crystal form A of Compound (I).
Figure 4:
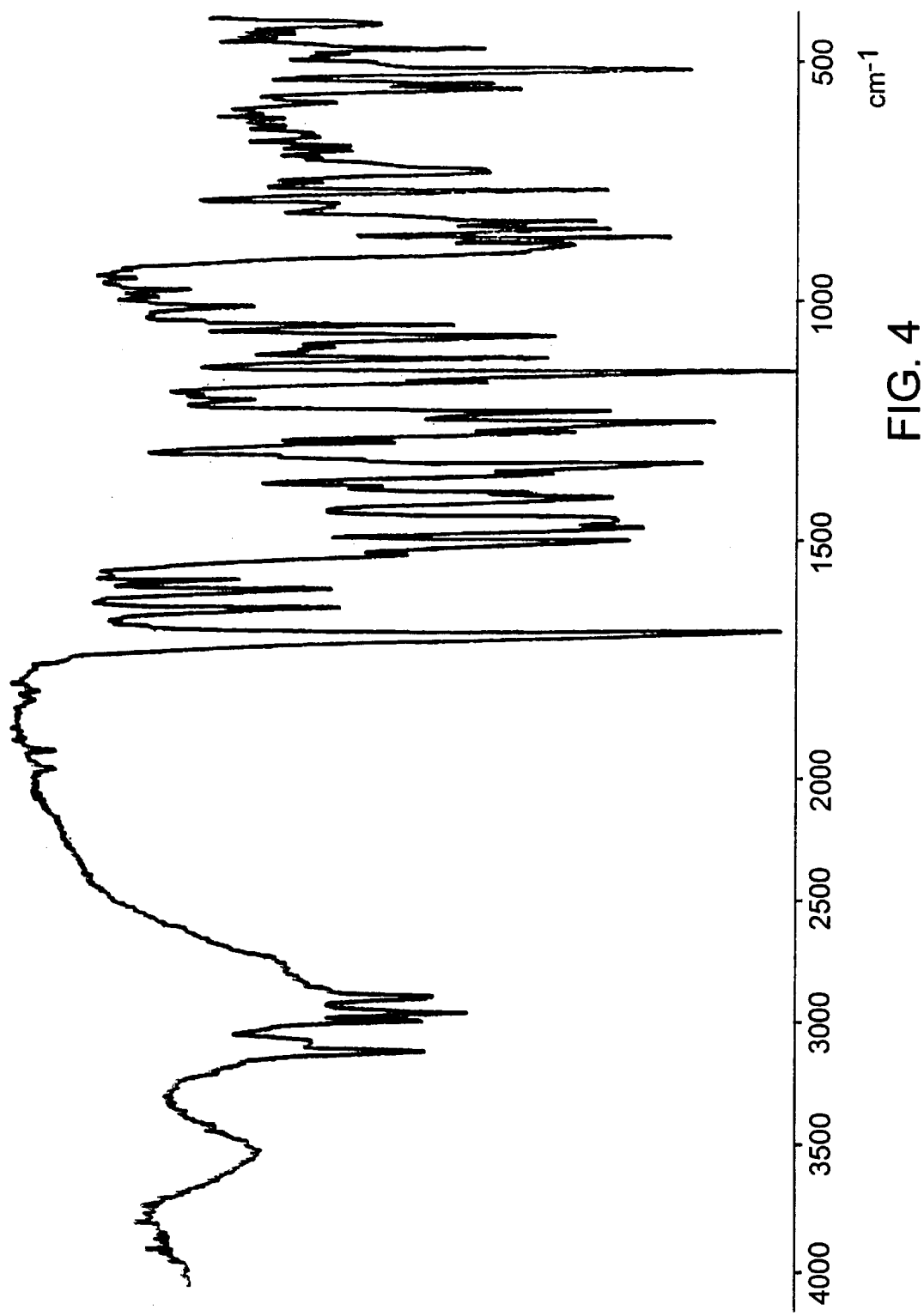
FIG. 4 shows an IR spectrum (KBr disk method) of crystal form B of Compound (I).
Figure 5:
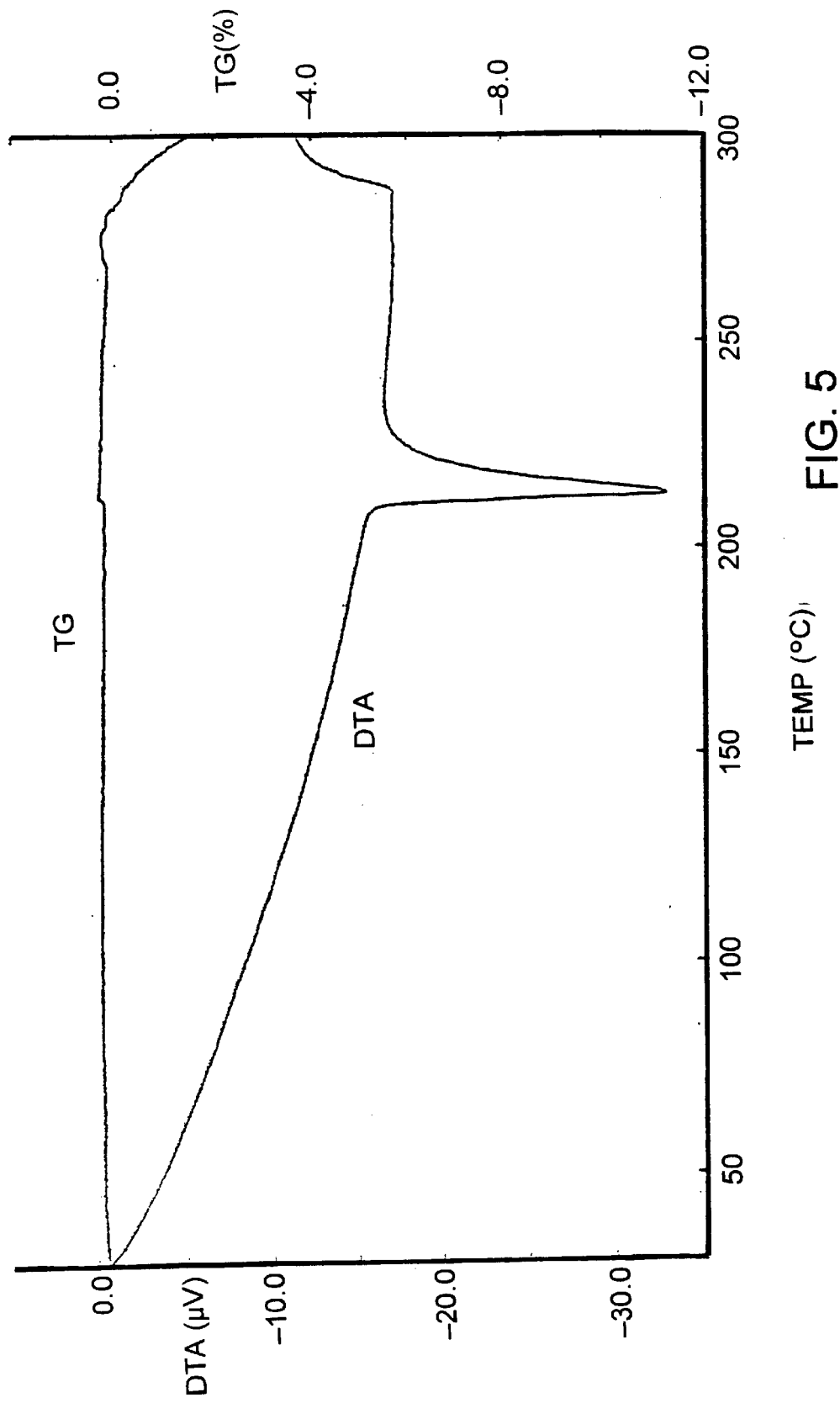
FIG. 5 shows a TG/DTA curve from thermogravimetry/differential thermal analysis of crystal form A of Compound (I).
Figure 6:
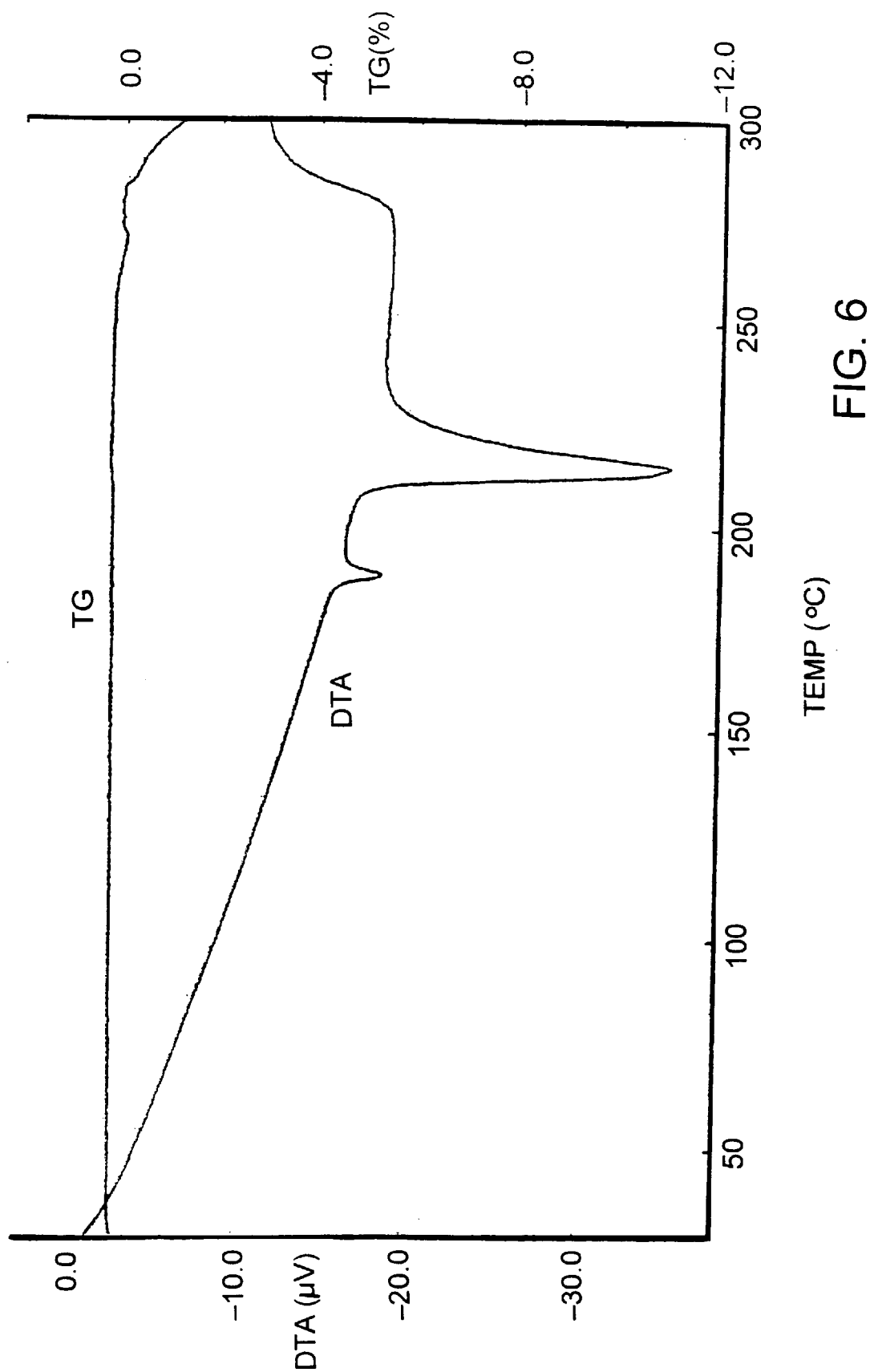
FIG. 6 shows a TG/DTA curve from thermogravimetry/differential thermal analysis of crystal form B of compound (I).

The present invention shall be described in detail below with reference to examples, but is not be construed as being limited thereto.

EXAMPLE 1

Production of Crystal Form B of 3-(2,4-dichlorobenzyl)-2-methyl-N-(pentylsulfonyl)-3H-benzimidazole-5-carboxamide 3-(2,4-Dichlorobenzyl)-2-methyl-N-(pentylsulfonyl)-3H-benzimidazole-5-carboxamide (110 g, 0.235 mol) was suspended in a solvent mixture of methanol (1100 g) and water (1100 g), into which an aqueous solution of 25% sodium hydroxide (38 g) was added, and subsequently the mixture was heated to 40° C. to dissolve the compound. After removing insoluble materials by filtration, the filtrate was heated up to 50° C., and a 10% aqueous solution (17 g) of hydrochloric acid was added drop-wise over 2 hours to precipitate crystals. This slurry of crystals was stirred at 50° C. for one hour for ripening, and subsequently a 10% aqueous solution of hydrochloric acid (68 g) was further added drop-wise over 4 hours to grow crystals. After the completion of the drop-wise addition, the slurry was cooled down to 25° C., and the crystals were collected by filtration. The wet crystals were washed with a mixed solvent of methanol (550 g) and water (550 g), and then vacuum-dried to obtain crystal form B of 3-(2,4-dichlorobenzyl)-2-methyl-N-(pentylsulfonyl)-3H-benzimidazole-5-carboxamide.

Yield was 102 g. IR spectrum of this product agreed with that known for crystal form B of 3-(2,4-dichlorobenzyl)-2-methyl-N-(pentylsulfonyl)-3H-benzimidazole-5-carboxamide.

EXAMPLE 2

Production of 3-(2,4-dichlorobenzyl)-2-methyl-N-(pentylsulfonyl)-3H-benzimidazole-5-carboxamide and the Crystal Form B Thereof A mixture of 3-(2,4-dichlorobenzyl)-2-methyl-3H-benzimidazole-5-carboxylic acid (34.1 g, 102 mmol), N,N'- carbonyldiimidazole (21.4 g) and N,N-dimethylformamide (122.7 g) was stirred for one hour at 35° C., into which 1-pentanesulfonamide (20.0 g) and 1,8-diazabicyclo[5.4.0]-7-undecene (20.1 g) were then added, and stirred for 6 hours at 40° C. After the reaction, a portion of N,N-dimethylformamide (62.9 g) was distilled off in vacuo, and, to the residue were added methanol (227.8 g) and water (227.8 g). This solution contained 1,8-diazabicyclo[5.4.0]-7-undecene and imidazole generated from N,N'-carbonyldiimidazole as the bases. This solution was filtered to remove insoluble materials, and the filtrate was heated to 50° C., and conc. hydrochloric acid (20.4 g) was added drop-wise thereto over one hour. After the dropping, crystal form B of 3-(2,4-dichlorobenzyl)-2-methyl-N-(pentylsulfonyl)-3H-benzimidazole-5-carboxamide (119 mg) was added as seed crystal, and the mixture was allowed to be ripen for 2 hours. After the ripening, conc. hydrochloric acid (15.5 g) was further added drop-wise thereto over 2 hours. The slurry was ripened for one hour at 50° C. and cooled down to 30° C., and then the crystals were collected by filtration. The crystals were washed with a mixed solvent of methanol (120 g) and water (120 g), and vacuum-dried to obtain crystal form B of 3-(2,4-dichlorobenzyl)-2-methyl-N-(pentylsulfonyl)-3H-benzimidazole-5-carboxamide.

Yield was 41.7 g. IR spectrum of this product agreed with that known for crystal form B of 3-(2,4-dichlorobenzyl)-2-methyl-N-(pentylsulfonyl)-3H-benzimidazole-5-carboxamide.

EXAMPLE 3

Production of Crystal Form A by Transition of Crystal Form B of 3-(2,4-dichlorobenzyl)-2-methyl-N-(pentylsulfonyl)-3H-benzimidazole-5-carboxamide Crystal form B of 3-(2,4-dichlorobenzyl)-2-methyl-N-(pentylsulfonyl)-3H-benzimidazole-5-carboxamide (5.0 g) was suspended in a mixed solvent consisting of acetone (51.2 g) and water (17.1 g), and the resulting slurry was stirred while heating at 40° C. About 4 hours later, crystals in the slurry completely transitioned into those with the IR spectrum that agreed with the spectrum of crystal form A of 3-(2,4-dichlorobenzyl)-2-methyl-N-(pentylsulfonyl)-3H-benzimidazole-5-carboxamide.

EXAMPLE 4

Production of Crystal Form A of 3-(2,4-dichlorobenzyl)-2-methyl-N-(pentylsulfonyl)-3H-benzimidazole-5-carboxamide A mixed solvent containing acetone (332.5 g) and water (42.0 g) was added to 3-(2,4-dichlorobenzyl)-2-methyl-N-(pentylsulfonyl)-3H-benzimidazole-5-carboxamide (35.0 g), and the mixture was heated under reflux to dissolve the crystals. This solution was filtered while being heated, and the filtrate was heated again under reflux, into which water (238 g) was added drop-wise over one hour while being heated under reflux. Crystals started to precipitate during the drop-wise addition of water. After the water addition was completed, the resulting slurry was cooled to 25° C., and the crystals were collected by filtration. The crystals were rinsed with a solvent mixture of acetone (87.2 g) and water (73.2 g), and then vacuum-dried to obtain crystal form A of 3-(2,4-dichlorobenzyl)-2-methyl-N-(pentylsulfonyl)-3H-benzimidazole-5-carboxamide.

Yield was 24.2 g. IR spectrum of this product agreed with that known for crystal form A of 3-(2,4-dichlorobenzyl)-2-methyl-N-(pentylsulfonyl)-3H-benzimidazole-5-carboxamide.

Industrial Applicability

Crystal form A of 3-(2,4-dichlorobenzyl)-2-methyl-N-(pentylsulfonyl)-3H-benzimidazole-5-carboxamide, a compound that has hypoglycemic activity or PDE5 inhibitory effect, is substantially and crystallographically stable and useful as a drug substance for medicines. On the other hand, crystal form B of 3-(2,4-dichlorobenzyl)-2-methyl-N-(pentylsulfonyl)-3H-benzimidazole-5-carboxamide can be efficiently purified by crystallization, since it forms larger crystals and can be very easily isolated by filtration. Thus, crystal form B is useful for purification of 3-(2,4-dichlorobenzyl)-2-methyl-N-(pentylsulfonyl)-3H-benzimidazole-5-carboxamide.

What is claimed is:

1. A substantially and crystallographically pure crystal form of 3-(2,4-dichlorobenzyl)-2-methyl-N-(pentylsulfonyl)-3H-benzimidazole-5-carboxamide having the following X-ray powder diffraction values (2θ), with an error range of ±0.2, in an X-ray powder diffraction assay using CuKα-ray as the characteristic X-ray:

Angle 2θ(°): about 4.7, about 9.5, about 10.5, about 15.6, and about 18.4.

2. A substantially and crystallographically pure crystal form of 3-(2,4-dichlorobenzyl)-2-methyl-N-(pentylsulfonyl)-3H-benzimidazole-5-carboxamide having the following X-ray powder diffraction values (2θ), with an error range of ±0.2, in an X-ray powder diffraction assay using CuKα-ray as the characteristic X-ray:

Angle 2θ(°): about 4.4, about 8.9, and about 13.4.

3. A pharmaceutical composition comprising, as an active ingredient, the crystal form of 3-(2,4-dichlorobenzyl)-2-methyl-N-(pentylsulfonyl)-3H-benzimidazole-5-carboxamide according to claim 1.

4. A pharmaceutical composition comprising, as an active ingredient, the crystal form of 3-(2,4-dichlorobenzyl)-2-methyl-N-(pentylsulfonyl)-3H-benzimidazole-5-carboxamide according to claim 2.

5. A process for producing a crystal form of 3-(2,4-dichlorobenzyl)-2-methyl-N-(pentylsulfonyl)-3H-benzimidazole-5-carboxamide (I), wherein said process comprises:

dissolving (I) in a solvent while heating said solvent to form a solution;

initiating a precipitation of a crystal form from the solution at 30° C. or higher; and obtaining a substantially and crystallographically pure crystal form of (I), wherein the X-ray powder diffraction values (2θ) of said crystal form of (I) in an X-ray powder diffraction assay using CuKα-ray as the characteristic X-ray and with an error range of ±0.2 are as follows:

Angle 2θ(°): about 4.7, about 9.5, about 10.5, about 15.6, and about 18.4.

6. The process as claimed in claim 5, wherein the solvent comprises an organic solvent or a mixture of an organic solvent and water.

7. The process as claimed in claim 5, wherein the precipitation of said crystal is initiated by a method selected from the group consisting of adding a second solvent to the solution, evaporating the organic solvent from the solution, and cooling the solution.

8. The process as claimed in claim 6, wherein the precipitation of said crystal is initiated by a method selected from the group consisting of adding a second solvent, evaporating the organic solvent from the solution, and cooling the solution.

9. A process for producing crystal form of 3-(2,4-dichlorobenzyl)-2-methyl-N-(pentylsulfonyl)-3H-benzimidazole-5-carboxamide (I), wherein said process comprises:

dissolving (I) in a solvent in the presence of a base and obtaining a solution;

initiating a precipitation of a crystal form from the solution; and obtaining a substantially and crystallographically pure crystal form of (I), wherein the X-ray powder diffraction values (2θ) of said crystal form of (I) in an X-ray powder diffraction assay using CuKα-ray as the characteristic X-ray and with an error range of ±0.2 are as follows:

Angle 2θ(°): about 4.4, about 8.9, and about 13.4.

10. The process as claimed in claim 9, wherein the solvent comprises an organic solvent or a mixture of organic solvent and water.

11. The process as claimed in claim 9, wherein the precipitation of the crystals is initiated done at a temperature of 60° C. or lower.

12. The process as claimed in claim 11, wherein the precipitation of the crystals is initiated done at a temperature of 60° C. or lower.

13. The process as claimed in claim 9, further comprises adding an acid to the solution.

* * * * *